United States Patent
Matzinger et al.

(10) Patent No.: US 6,168,957 B1
(45) Date of Patent: Jan. 2, 2001

(54) DIAGNOSTIC TEST STRIP HAVING ON-STRIP CALIBRATION

(75) Inventors: David Matzinger, Menlo Park; Ian Harding, San Mateo; Michael O'Neil, Sunnyvale, all of CA (US)

(73) Assignee: Lifescan, Inc., Milpitas, CA (US)

( * ) Notice: Under 35 U.S.C. 154(b), the term of this patent shall be extended for 0 days.

(21) Appl. No.: 08/881,985

(22) Filed: Jun. 25, 1997

(51) Int. Cl.[7] .................................................. G01N 33/543
(52) U.S. Cl. .............................. 436/518; 422/56; 422/57; 422/58; 422/61; 435/7.9; 435/14; 435/28; 435/287.1; 435/287.2; 435/287.7; 435/287.8; 435/805; 435/810; 435/970; 436/514; 436/169; 436/170; 436/805; 436/810; 436/815
(58) Field of Search ........................ 422/56, 57, 58, 422/61; 435/7.9, 14, 28, 287.1, 287.2, 287.7, 287.8, 805, 810, 970; 436/514, 518, 169, 170, 805, 810, 815

(56) References Cited

U.S. PATENT DOCUMENTS 3,907,503  9/1975  Betts et al. .......................... 23/253 R
4,144,306 * 3/1979  Figueras ................................. 422/56
4,476,149  10/1984  Poppe et al. ............................. 427/2
4,510,383  4/1985  Ruppender .............................. 235/462
4,592,893  6/1986  Poppe et al. ............................ 422/56
4,877,580 * 10/1989  Aronowitz et al. .................... 436/170
4,935,346  6/1990  Phillips et al. ........................... 435/14
5,281,395  1/1994  Markart et al. ..................... 422/82.05
5,515,170  5/1996  Matzinger et al. .................... 356/423
5,563,031  10/1996  Yu ............................................ 435/4

FOREIGN PATENT DOCUMENTS 0 256 806     2/1988   (EP) ............................. C01Q 1/54
0 290 610    11/1988   (EP) ............................. G01N 33/52
01006865     1/1989    (JP) ............................. G01N 33/96
WO96/13707   5/1996    (WO) .

* cited by examiner

Primary Examiner—Christopher L. Chin
(74) Attorney, Agent, or Firm—James Riesenfeld

(57) ABSTRACT

A dry phase reagent test strip for measuring the concentration of an analyte in a biological fluid includes a colored indicator whose hue indicates a calibration of the strip. Preferably, the test strip measures the concentration of glucose in whole blood.

4 Claims, 2 Drawing Sheets

DIAGNOSTIC TEST STRIP HAVING ON-STRIP CALIBRATION

BACKGROUND OF THE INVENTION

1. Field of the Invention

This invention relates to a dry phase test strip for measuring the concentration of an analyte in a biological fluid; more particularly, a strip that has built-in calibration.

2. Description of the Related Art

Dry phase reagent test strips incorporating enzyme-based compositions are used extensively in clinical laboratories, physicians' offices, hospitals, and homes to measure the concentration of certain analytes in biological fluids. These strips have, for example, measured glucose, cholesterol, proteins, ketones, phenylalanine, or enzymes in blood, urine, or saliva. Measuring glucose concentration in samples of whole blood is a particularly common use. In fact, reagent strips have become an everyday necessity for many of the nation's several million people with diabetes. Since diabetes can cause dangerous anomalies in blood chemistry, it can contribute to vision loss, kidney failure, and other serious medical consequences. To minimize the risk of these consequences, most people with diabetes must test themselves periodically, then adjust their glucose concentration accordingly, for instance, through diet, exercise, and/or with insulin injections. Some patients must test their blood glucose concentration as often as four times or more daily.

It is especially important for persons who must control their diet in order to regulate sugar intake and/or administer insulin injections, and who must be guided in this regard by frequent tests of blood glucose concentration, to have a rapid, inexpensive, and accurate test.

Test strips are known that contain a testing reagent that turns a different shade of color, depending on the concentration of glucose in a blood sample that has been applied to the strip. The blood glucose concentration is measured by inserting a strip into a meter that is basically a reflectance photometer, which determines the concentration from the change in color caused by the reaction between the testing reagent and blood glucose. The testing reagent typically contains an enzyme, such as glucose oxidase, which is capable of oxidizing glucose to gluconic acid lactone and hydrogen peroxide; an oxidizable dye; and a substance having peroxidative activity, which is capable of selectively catalyzing oxidation of the oxidizable dye in the presence of hydrogen peroxide. (See, for example, U.S. Pat. No. 4,935,346, issued Jun. 19, 1990, to Phillips et al.)

Whether the test is conducted in the home, physician's office, clinic or hospital, accuracy and reproducibility of the glucose determination are extremely important. However, these strips, by their nature, do not lend themselves to large-scale manufacture with adequate strip-to-strip reproducibility from one batch to the next. Consequently, it is necessary to assign to each lot of strips a calibration code that corrects for this variability. The calibration code may be marked on the strip container, and the user must enter the code into the meter when he or she begins to use a new batch of strips. If the user fails to enter a new calibration code or enters an incorrect one, the resulting value of glucose will be incorrect. Thus, it is advantageous to incorporate the calibration code on the strip, so that the meter can "read" the calibration code before calculating the glucose concentration. In that way, there is no involvement of the user, who typically is unaware that calibration is needed.

U.S. Pat. No. 4,476,149, issued on Oct. 9, 1984, to Poppe et al., discloses an analysis test strip and process for making it that includes on-strip calibration information. The strip includes a "test field" in which the analysis takes place and a batch-specific bar code, which provides calibration information specific to strips made in a particular batch. (See also U.S. Pat. Nos. 4,510,383 and 4,592,893.) In principle, the process provides a strip whose calibration is "transparent" to the user; i.e., the user is unaware of the calibration step. While that is a highly desirable result, it comes at a high price. The bar code must be printed very precisely, with tight tolerances on the width and spacing of the bars, over the entire length of the web that constitutes a single batch of (uncut) strips. Moreover, the printing must be done in a way that does not change the characteristics of the test field. Furthermore, the meter must have a sophisticated optical system in order to read the tightly-spaced bar code reliably (See U.S. Pat. No. 4,510,383).

U.S. Pat. No. 5,281,395, issued on Jan. 25, 1994, to Markart et al., discusses the practical problems raised by the strip of Poppe, et al. and addresses some of them with a two-strip system. The "test carrier" contains the reagent for reacting with the analyte to be measured and the "code carrier" has the calibration bar code that is characteristic of a particular batch. Each carrier also has a machine-readable batch identification. This approach reduces the technical difficulties and expense involved in manufacturing the strips of Poppe et al; however, it requires the use of a second strip in order to calibrate the meter.

U.S. Pat. No. 3,907,503, issued on Sep. 23, 1995, to Betts et al., discloses a test system for measuring a variety of analytes, using a single strip. The strip includes a code means that identifies the particular test device and one or more reagents for the particular tests done by that strip. The code means does not provide a calibration for any of the reagent systems. In its simplest form, it is an opaque area attached to a generally transparent carrier. The nature of the test device is identified by the position of the code means relative to the reagent test areas. The code means may also include a distinctive mark or color, which can be recognized by the meter as identifying a particular type of strip.

Connolly, in PCT Application WO96/13707, published on May 9, 1996, discloses an apparatus and method for detecting various analytes in body fluids, using dry test strips. In one embodiment, test strips are color coded to identify the test that a particular strip is intended for. Thus, a blue strip may measure glucose and a red strip cholesterol. The colors are divided into shades, for example 64 shades of blue represent 64 different lot numbers of glucose strips. The apparatus has a memory module which stores a lot number. If the lot number measured from the strip doesn't match the lot number in the memory module, the test isn't performed. This approach requires that each batch of test strips have a memory module, which is inserted into the apparatus before the strips of that batch can be used.

U.S. Pat. No. 5,515,170, issued on May 7, 1996, to Matzinger et al., discloses a reagent strip for measuring the concentration of glucose in whole blood. The strip has a testing pad that contains a reagent system that changes color to indicate the glucose concentration. The testing pad is formed from an anisotropic membrane, which has relatively large pores near one major surface and smaller pores near the opposite surface. A porous transport medium is attached to the large-pore surface of the pad. The whole blood sample is applied to the transport medium, which transfers a detectable portion of the sample to the large-pore side of the pad. Glucose in the sample then moves toward the opposite side, where it reacts with the reagent to cause a color change that is visible from the small-pore side of the pad and that indicates the glucose concentration in the sample.

There is a need for a reliable system that incorporates calibration code information on a strip in a way that does not make excessive demands on the strip-manufacturing process, yet eliminates the need for a user to be involved in calibration.

SUMMARY OF THE INVENTION

In accordance with the present invention a diagnostic test strip for measuring an analyte concentration in a sample of biological fluid, comprises
- (a) a membrane, having a sample side, to which the fluid sample is applied, and a testing side, opposite the sample side;
- (b) a testing reagent impregnated in the membrane for reacting with the analyte in the sample to cause a detectable color change on the testing side; and
- (c) a membrane support, attached to the membrane and having on a major surface a colored indicator, whose hue indicates calibration of the strip.

In a method of the present invention, a method for measuring an analyte concentration in a sample of biological fluid, comprises the steps of
- (a) providing a test strip that includes
  - (i) a membrane having a sample side and a testing side, opposite to it,
  - (ii) a testing reagent impregnated in the membrane for reacting with the analyte to cause a color change on the testing side, and
  - (iii) a membrane support having on a major surface a colored indicator, whose hue indicates a calibration of the strip.
- (b) applying the fluid sample to the sample side of the membrane,
- (c) measuring the hue of the indicator and the change in color of the testing side, and
- (d) calibrating the analyte concentration from the measured values of indicator hue and testing side color change.

A diagnostic test strip of the present invention eliminates the need for a user to enter a strip calibration code into a meter and thereby eliminates the possibility that an incorrect code could be entered.

DETAILED DESCRIPTION OF THE INVENTION

Figure 1:
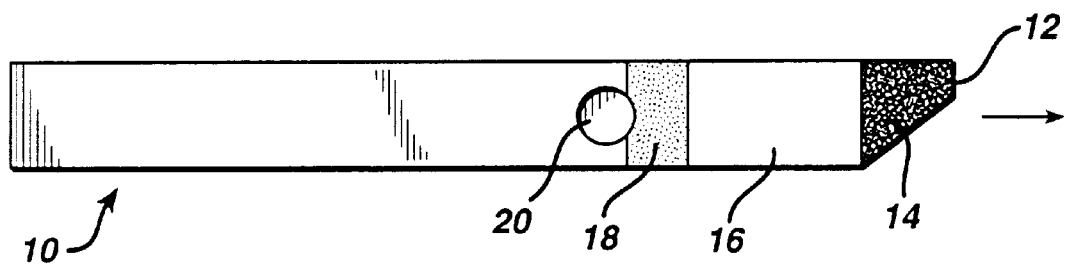
FIGS. 1 and 1A are a plan view of a strip of the present invention.
Figure 1A:
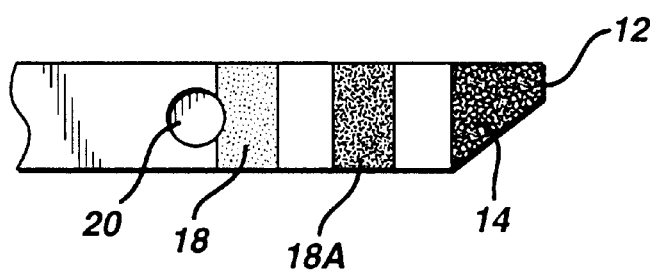

The present invention provides an indicator on the type of diagnostic test strip that is used in conjunction with a meter to measure analyte concentration in a sample of biological fluid. The indicator is colored, and its hue indicates to the meter a calibration that is characteristic of the strip and that enables the meter to compute the analyte concentration more accurately than is possible without the calibration information. By "hue" in this specification and the appended claims, we mean the characteristic of a substance which results from its selective absorption of certain wavelengths of visible light in preference to others. Thus, hue is distinguished from "shade," which has reference to the general absorption of a substance throughout the visible spectrum, dark shades absorbing more, light shades absorbing less.

The present indicator is adapted for use on any test strips used to measure the concentration of an analyte. It is useful where strip parameters have a variability that can be reduced by incorporating a calibration code into the computation of the analyte concentration. Since the indicator involves a color measurement, it is particularly well adapted for systems that incorporate an optical measurement system that can also be used to read the indicator. Photometric systems for monitoring blood glucose are an example, since these measure a color change in a reagent in order to determine glucose concentrations in whole blood.

A photometric strip-and-meter system that is suitable for the present invention involves a two-layer strip of the type described by Matzinger et al. in U.S. Pat. No. 5,515,170, incorporated herein by reference. The key elements of such a strip are a porous membrane that incorporates a testing reagent, a porous transport medium attached to one side of the membrane, and a support layer attached to the other side. An aperture through the support layer provides a view of the membrane. A blood sample is applied to the transport medium and a portion of it travels to and through the membrane. The strip undergoes a measurable color change in response to glucose in the blood sample. The transport medium is adapted to accept a whole blood sample and transport a detectable portion of the sample to the membrane. The sample may be moved by capillary action. The transport medium preferably extends past one or more ends of the membrane so as to form a reservoir for holding excess amounts of blood sample. Accordingly, it is preferred that the transport medium be capable of holding from about 10 to about 50 microliters of blood, preferably about 35 microliters of blood, and of passing from about 3 to about 10 microliters of blood to the membrane. The transport medium may be composed of natural fibers, such as cotton or paper, as well as polyesters, polyamides, polyethylene, and other synthetic polymers. Polyethylene is the preferred transport medium material; for example, porous polyethylene available from the Porex Corp. of Fairburn, Ga.

The membrane may be of a uniform composition or may be a coated substrate. It has a sample side, to which the transport medium is attached, and a testing side, where the color change is observed. Preferably, the membrane is anisotropic; more preferably, having a broad range of pore sizes. For example, a gradient of pore sizes in which the ratio of largest-to-smallest pores is in the range of about 100–400 is preferred. On the testing side of the membrane, where the pores are smallest, the void volume is relatively small, and the material of the membrane is generally quite dense, within a layer that can typically constitute up to 20% of the membrane's thickness. Within this layer, pore size is preferably in the range from about 0.1 to about 0.8 micrometer, with a nominal pore size preferably about 0.3–0.4 micrometers. On the sample side, pore size is preferably in the range from about 40 micrometers to about 125 micrometers. After passing through the transport medium, the blood enters the sample side of the membrane and encounters increasingly smaller pores as it penetrates through the membrane. Eventually, solids such as red blood cells reach a position in the membrane where they can penetrate no further. The balance of the sample, still containing the dissolved glucose, penetrates through to the testing side. The anisotropic nature of the membrane permits relatively rapid flow rates through the membrane, even while filtration of the solids is taking place. Polysulfones and polyamides (nylons) are examples of suitable membrane materials.

As the sample passes through the membrane, reaction with the reagent causes a light-absorbing dye to be formed in the void volume near the testing side, thereby substantially affecting reflectance from the membrane.

The testing reagent comprises a component for converting glucose to hydrogen peroxide and a component for detecting hydrogen peroxide. The reagent may optionally further comprise a separating component which causes solids, such as red blood cells, to become attached to or entrapped in the membrane, effectively removing the solids from the biological fluid.

A preferred component for converting glucose to hydrogen peroxide is glucose oxidase, an enzyme that reacts with glucose and oxygen to produce gluconolactone and hydrogen peroxide.

The hydrogen peroxide so produced reacts with the component for detecting hydrogen peroxide, which comprises a peroxidase that selectively catalyzes a reaction between the hydrgen peroxide and an indicator. Horseradish peroxidase is an especially preferred peroxidase catalyst and [3-methyl-2-benzo-thiazolinone hydrazone] N-fulfonyl benzene-sulfonate monosodium (MBTHSB) combined with 8-anilino-1 naphthalene sulfonic acid ammonium (ANS) is a preferred indicator dye couple to react with the hydrogen peroxide.

Details concerning the reagent and other elements of the strip appear in U.S. Pat. No. 5,563,031, issued on Oct. 8, 1996, to Y. Yu, which is incorporated herein by reference.

The color change on the testing side of the membrane is measured by an optical sensor (i.e., by reflectance photometry) to yield the blood glucose concentration. One or more calibrated reference color guides are exposed to a light source before or after the testing side is exposed to the light source. For example, light may be sequentially reflected to a sensor from the color guide and the testing side.

The sensor generates a signal that changes as the reference and the testing side are sequentially exposed to the light source. The changes in signal are then quantitatively related to concentration levels of glucose in the sample according to mathematical formulas which have previously been prepared using similar viewing means and samples of known glucose concentration. Details of this embodiment appear in copending U.S. patent application Ser. No. 493,435, filed on Jun. 22, 1995, and incorporated herein by reference.

FIG. 1. is a plan view that illustrates an on-strip calibration indicator on the diagnostic test strip described above. The surface 10 which appears in FIG. 1 (the "bottom" or "testing" surface) is that which faces the reflectance photometer when the strip is inserted into the meter. The direction of insertion is indicated by the arrow. From the leading edge 12, dark zone 14 extends to light standard zone 16. Indicator 18 is colored, the hue indicating a calibration code that is used by a meter, together with the reflected signal from the testing side 20 of the membrane to calculate a glucose concentration.

Figure 2:
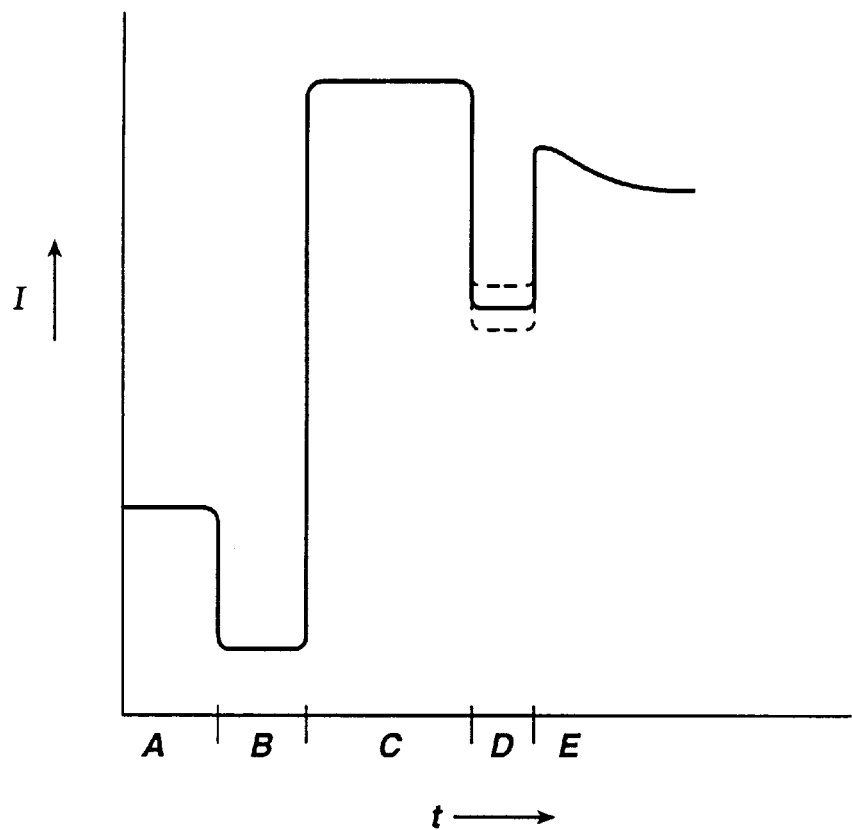
FIG. 2 depicts light intensity as a function of time during insertion of the strip of FIG. 1 into a meter.

In practice, a user applies a whole blood sample to the "top" or "sample" side of the membrane, opposite the side shown in FIG. 1. Thereafter, as strip 10 is inserted into a meter there is a sequence of reflected light that provides a "signature" for the strip and that initiates the glucose measurement. The sequence is shown schematically in FIG. 2, which depicts reflected light intensity, I, as a function of time as the strip is inserted. Initially, in region A, the sensor detects light reflected from the empty strip holder. The reduced intensity in region B indicates that a strip is being inserted and the reflection is from dark zone 14. As strip insertion continues, increased intensity in region C indicates that light is being reflected from standard zone 16. Next, reflected light intensity is again reduced in region D, as the sensor detects reflection from indicator 18. The dashed lines show that the reflected intensity, as well as the intensity at a second wavelength, will differ from one strip to the next to provide calibration information. Finally, in region E, when the strip is fully inserted, the sensor detects an initially increased light intensity reflected from the testing side 20 of the membrane. As the glucose reaction proceeds, dye formation causes a reduction in reflected light to a value that indicates the glucose concentration in the sample. The calculation of the value involves the calibration, provided by reflection in region D, and the quantity of dye formation, provided by reflection in region E. Note that we refer above to reflected light; however, indicator 18 could alternatively be transparent, and calibration information would result from differences in absorbance of light incident on the other side of the strip.

Figure 3:
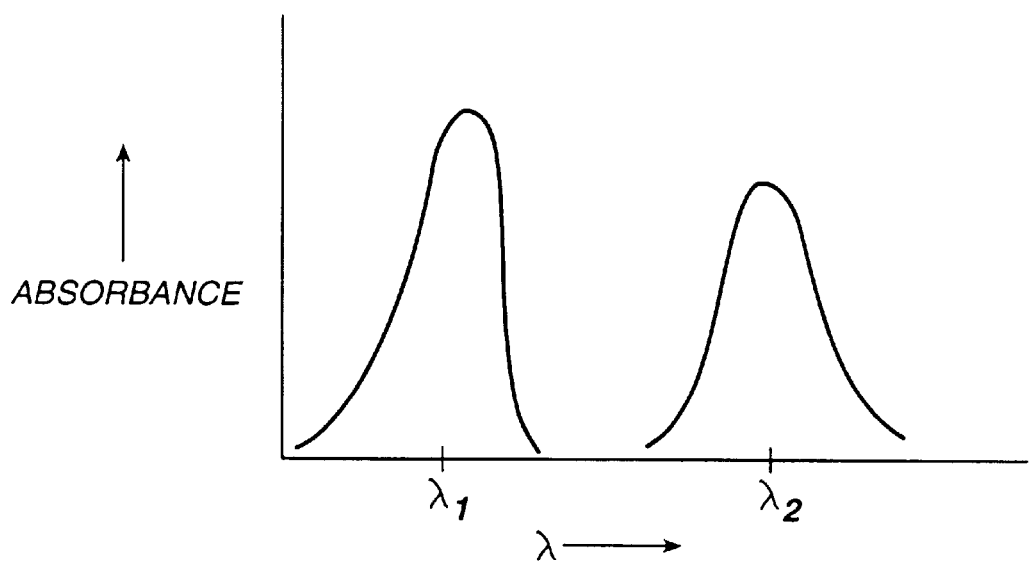
FIG. 3 depicts a schematic of absorption spectra of dyes suited for use in this invention.

In order to provide accurate calibration, a large number of calibration codes is desirable. To provide such a large number and to reduce the risk of the meter sensing the wrong code, light reflected from indicator 18 is measured at two wavelengths, and the ratio of the two values of reflected light provides the calibration information. This is accomplished by printing indicator 18 using variable combinations of two different inks and illuminating the indicator with two different colors of light. Ideally, the indicator is colored by inks that have narrow regions of selective absorption, such as is depicted schematically in FIG. 3. As shown there, one ink has an absorption peak at $\lambda_1$, the other at $\lambda_2$, and each ink shows little absorption at the peak absorption wavelength of the other. Similarly, the light sources would ideally have outputs with peaks that correspond to the absorption peaks of the inks. As a practical matter, it is neither possible nor necessary to achieve these ideals. For example, with the strip and meter system described above, it is convenient to use a meter having two LEDs whose peak outputs are at about 660 nm and 940 nm, respectively. This meter simply requires that the indicator code use inks that have very different absorption at those two wavelengths.

The indicator code that is appropriate for a particular batch of strips is determined by the membrane batch, since it is the membrane that cannot be made sufficiently uniform from one batch to the next. Thus a small number of trial strips are made from a membrane batch and the appropriate calibration code is determined. That code is then applied to each of the strips prepared from that membrane batch, by applying the appropriate ratio of ink amounts at the indicator position 18. The inks can be applied in any of a variety of ways well known in the art; e.g., lithography, screen printing, electrographic printing, 19 laser printing, and ink-jet printing. Ink-jet printing is preferred.

Figure 4:
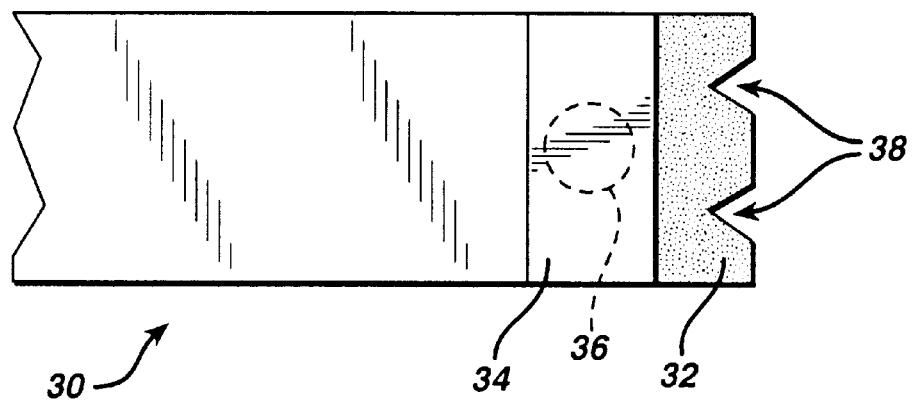
FIG. 4 is a plan view of another embodiment of a strip of the present invention.

FIG. 4 depicts another embodiment of a strip of this invention. This embodiment is described in detail in U.S. Pat. No. 5,304,468, issued on Apr. 19, 1994, to Phillips et al., incorporated herein by reference. Its operation is summarized below. A strip 30 has an indicator region 32 that provides calibration information and membrane 34, which is impregnated with a reagent that reacts with an analyte to cause a color change. As with the strip depicted in FIG. 1, the analyte-containing sample is applied to the strip on the opposite side of the membrane—shown here by the dashed circle surrounding sample application area 36. Notches 38 ensure proper placement of strip 30 in a meter. The strip shown in FIG. 4 is of the type that is first placed into a meter, before the sample (e.g., blood) is applied. Blood penetrating though membrane 34 is detected by the meter, and a timed sequence is begun, at the end of which the reflection is measured and the analyte concentration calculated from that measurement.

This sequence differs from that followed with the embodiment of FIG. 1, where the sample is applied to the strip before it is inserted into the meter. The fact that the sample is applied after the strip is inserted means that there is generally no need to measure reflected light from any area of the strip other than the reaction area, unlike the situation with the strip of FIG. 1 (see FIG. 2, above). Nevertheless, reflection from indicator region 32 could be read in a variety of ways. For example, a switch electrical, electromechanical, or optical—could be triggered when the strip is inserted, and reflection from region 32 could be measured as the strip is inserted into the meter. Alternatively, a switch could be triggered as the strip is withdrawn; however, that would require a user to withdraw the strip from the meter before the analyte concentration could be calculated. As with the embodiment of FIG. 1, the calibration of a strip batch is determined from sample strip formed using a particular membrane batch and the calibration is printed in the form of an area 32 of a particular hue. For the strip and meter of this embodiment, it is convenient to use a meter that measures reflected light from the strip at 635 nm and 700 nm, but other wavelengths could be used instead.

We claim:

1. A diagnostic test strip for measuring an analyte concentration in a sample of biological fluid, comprising (a) a membrane, having a sample side, to which the fluid sample is applied, and a testing side, opposite the sample side;

(b) a testing reagent impregnated in the membrane for reacting with the analyte in the sample to cause a detectable color change on the testing side; and (c) a membrane support, attached to the membrane and having on a major surface a colored indicator, whose hue indicates a calibration of the strip.

2. The strip of claim 1 in which the analyte is glucose and the fluid is whole blood.

3. The strip of claim 2 in which the reagent comprises (a) a first component for creating hydrogen peroxide from glucose and oxygen and (b) a second component for reacting with the hydrogen peroxide to cause the color change on the testing side.

4. The strip of claim 1 in which the indicator is colored by a combination of two dyes, and the hue is determined by the relative amounts of the dyes.

* * * * *